(12) United States Patent
Weichselbaum et al.

(10) Patent No.: US 7,537,894 B2
(45) Date of Patent: May 26, 2009

(54) METHODS AND KITS FOR MONITORING BARRETT'S METAPLASIA

(75) Inventors: Ralph Weichselbaum, Chicago, IL (US); Nikolai Khodarev, Villa Park, IL (US); Eric Kimchi, Hershey, PA (US); Mitchell Posner, Chicago, IL (US)

(73) Assignee: The University of Chicago, Chicago, IL (US)

( * ) Notice: Subject to any disclaimer, the term of this patent is extended or adjusted under 35 U.S.C. 154(b) by 91 days.

(21) Appl. No.: 11/367,602

(22) Filed: Mar. 2, 2006

(65) Prior Publication Data

US 2006/0199210 A1 Sep. 7, 2006

Related U.S. Application Data

(60) Provisional application No. 60/658,424, filed on Mar. 2, 2005.

(51) Int. Cl.
*C12Q 1/68* (2006.01)
(52) U.S. Cl. .......................................... 435/6; 536/24.5
(58) Field of Classification Search ....................... None
See application file for complete search history.

(56) References Cited

OTHER PUBLICATIONS

Reid et al. Gastrointest Endosc. Clin. N. Am. vol. 13(2), pp. 369-397, 2003). Abstract only.*
Tockman et al. Cancer Research, vol. 52, pp. 2711s-2718s, 1992.*
Chang et al. (World J. Gastroenterol, vol. 10(21), pp. 3194-3196, 2004).*
Yoshida et al. (FEBS Letter, vol. 414(2), pp. 333-337, 1997) Abstract only.*
Kimos et al. (Int. J. Cancer, vol. 111, pp. 415-417, 2004).*
Barrett, M.T. et al., "Transcriptional analyses of Barrett's metaplasia and normal upper GI mucosae," Neoplasia (2002) 4:121-128.
Basson, C.T. et al., "Identification, characterization, and chromosomal localization of the human homolog (hES) of ES/130," Genomics (1996) 35:628-631.
Capo-Chichi, C.D. et al., "Anomalous expression of epithelial differentiation-determining GATA factors in ovarian tumorigenesis," Cancer Res. (2003) 63:4967-4977.
Care, A. et al., "HOXB7: a key factor for tumor-associated angiogenic switch," Cancer Res. (2001) 61:6532-6539.
Chen, Y.J. et al., "Loss of heterozygosity of chromosome 1q in gastrinomas: occurrence and prognostic significance," Cancer Res. (2003) 63:817-823.
Dahlberg, P.S. et al., "Gene expression profiles in esophageal adenocarcinoma," Ann. Thorac. Surg. (2004) 77:1008-1015.
Devesa, S.S. et al., "Changing patterns in the incidence of esophageal and gastric carcinoma in the United States," Cancer (1998) 83:2049-2053.
Ding, M. et al., "C. elegans ankyrin repeat protein VAB-19 is a component of epidermal attachment structures and is essential for epidermal morphogenesis," Development (2003) 130:5791-5801.
Draghici, S. et al., "Global functional profiling of gene expression," Genomics (2003) 81:98-104.

Elder, J.T. et al., "Evidence for local control of gene expression in the epidermal differentiation complex," Exp. Dermatol. (2002) 11:406-412.
Garcia-Cao, M. et al., "Epigenetic regulation of telomere length in mammalian cells by the Suv39h1 and Suv39h2 histone methyltransferases," Nat. Genet. (2004) 36:94-99.
Goldblum, J.R. et al., "Dysplasia arising in Barrett's esophagus: diagnostic pitfalls and natural history," Semin. Diag. Pathol. (2002) 19:12-19.
Hitomi, K. et al., "Analysis of epidermal-type transglutaminase (transglutaminase 3) in human stratified epithelia and cultured keratinocytes using monoclonal antibodies," J. Dermatol. Sci. (2003) 32:95-103.
Kalinin, A.E. et al., "Epithelial barrier function: assembly and structural features of the cornified cell envelope," Bioessays (2002) 24:789-800.
Kaufman, C.K. et al., "GATA-3: an unexpected regulator of cell lineage determination in skin," Genes Dev. (2003) 17:2108-2122.
Khodarev, N.N. et al., "Interaction of amifostine and ionizing radiation on transcriptional patterns of apoptotic genes expressed in human microvascular endothelial cells (HMEC)," Int. J. Rad. Oncol. Biol. Phys. (2004) 60:553-563.
Khodarev, N.N. et al., "Method of RNA purification from endothelial cells for DNA array experiments" Biotechniques (2002) 32:316-320.
Khodarev, N.N. et al., "Receiver operating characteristic analysis: a general tool for DNA array data filtration and performance estimation," Genomics (2003) 81:202-209.
Khodarev, N.N. et al., "STAT1 is overexpressed in tumors selected for radioresistance and confers protection from radiation in transduced sensitive cells," PNAS USA (2004) 101:1714-1719.
Kitajima, Y., "Mechanisms of desmosome assembly and disassembly," Clin. Exp. Dermatol. (2002) 27:684-690.
Koh, K. et al., "ELT-5 and ELT-6 are required continuously to regulate epidermal seam cell differentiation and cell fusion in C. elegans," Development (2001) 128:2867-2880.
Koon, N. et al., "Clustering of molecular alterations in gastroesophageal carcinomas," Neoplasia (2004) 6:143-149.
La Celle, P.T. et al., "Human homeobox HOXA7 regulates keratinocyte transglutaminase type 1 and inhibits differentiation," J. Biol. Chem. (2001) 276:32844-32853.
Lagergren, J. et al., "Symptomatic gastroesophageal reflux as a risk factor for esophageal adenocarcinoma," N. Eng. J. Med. (1999) 34:825-831.
Luo, A. et al., "Discovery of Ca2+-relevant and differentiation associated genes downregulated in esophageal squamous cell carcinoma using cDNA microarray," Oncogene (2004) 23:1291.
Mahy, N.L. et al., "Gene density and transcription influence the localization of chromatin outside of chromosome territories detectable by FISH," J. Cell Biol. (2002) 159:753-763.
Marenholz, I. et al., "Identification of human epidermal differentiation complex (EDC)-encoded genes by substractive hybridization of entire YACs to a gridded keratinocyte cDNA library," Genome Res. (2001) 11:341-355.

(Continued)

*Primary Examiner*—Larry R. Helms
*Assistant Examiner*—Meera Natarajan
(74) *Attorney, Agent, or Firm*—Michael Best & Friedrich LLP

(57) ABSTRACT

Disclosed are methods and kits for assessing risk of progression of Barrett's esophagus to adenocarcinoma.

7 Claims, 3 Drawing Sheets

OTHER PUBLICATIONS

McManus, D.T. et al., "Biomarkers of esophageal adenocarcinoma and Barrett's esophagus," Cancer Res. (2004) 64:1561-1569.

Merrill, B.J. et al., "Tcf3 and Lef1 regulate lineage differentiation of multipotent stem cells in skin," Genes Dev. (2001) 15:1688-1705.

Naora, H. et al., "A serologically identified tumor antigen encoded by a homeobox gene promotes growth of ovarian epithelial cells," Proc. Natl. Acad. Sci. USA (2001) 98:4060-4065.

Neglia, M. et al., "Amplification of the pericentromeric region of chromosome 1 in a newly established colon carcinoma cell line," Cancer Genet. Cytogenet. (2003) 142:99-106.

Pantou, D. et al., "Cytogenetic profile of unknown primary tumors: clues for their pathogenesis and clinical management," Neoplasia (2003) 5:23-31.

Sarkar, S. et al., "A novel ankyrin repeat-containing gene (Kank) located at 9p24 is a growth suppressor of renal cell carcinoma," J. Biol. Chem. (2002) 277:36585-36591.

Seery, J.P., "Stem cells of the oesophageal epithelium," J. Cell Sci. (2002) 115:1783-1789.

Shaheen, N. et al., "Gastroesophageal reflux, Barrett esophagus and esophageal cancer," JAMA (2002) 287:1972-1981.

Shaheen, N.J. et al., "Is there publication bias in the reporting of cancer risk in Barrett's esophagus?" Gastroenterology (2000) 119:333-338.

Stein, H.J. et al., Barrett's esophagus: pathogenesis, epidemiology, function abnormalities, malignant degeneration, and surgical management, Dysphagia (1993) 8:276-288.

Stelnicki, E.J. et al., "HOX homeobox genes exhibit spatial and temporal changes in expression during human skin development," J. Invest. Dermatol. (1998) 110:110-115.

Swisher, S.G. et al., "Changes in the surgical manangement of esophageal cancer from 1970 to 1993," Am. J. Surg. (1995) 169:609-614.

Sy, S.M. et al., "distinct patterns of genetic alterations in adenocarcinoma and squamous cell carcinoma of the lung," Eur. J. Cancer (2004) 40:1082-1094.

Tusher, V.G. et al., "Significance analysis of microarrays applied to the ionizing radiation response," PNAS USA (2001) 98:5116-5121.

Volpi, E.V. et al., "Large-scale chromatin organization of the major histocompatibility complex and other regions of human chromosome 6 and its response to interferon in interphase nuclei," J. Cell Sci (2000) 113:1565-1576.

Williams, R.R. et al., "Subchromosomal positioning of the epidermal differentiation complex (EDC) in keratinocyte and lymphoblast interphase nuclei," Exp. Cell Res. (2002) 272:163-175.

Wong, N. et al., "Positional mapping for amplified DNA sequences on 1q21-q22 in hepatocellular carcinoma indicates candidate genes over-expression," J. Hepatol. (2003) 38:298-306.

Xu, Y. et al., "Artificial neural networks and gene filtering distinguish between global gene expression profiles of Barrett's esophagus and esophageal cancer," Cancer Res. (2002) 62:3493-3497.

* cited by examiner

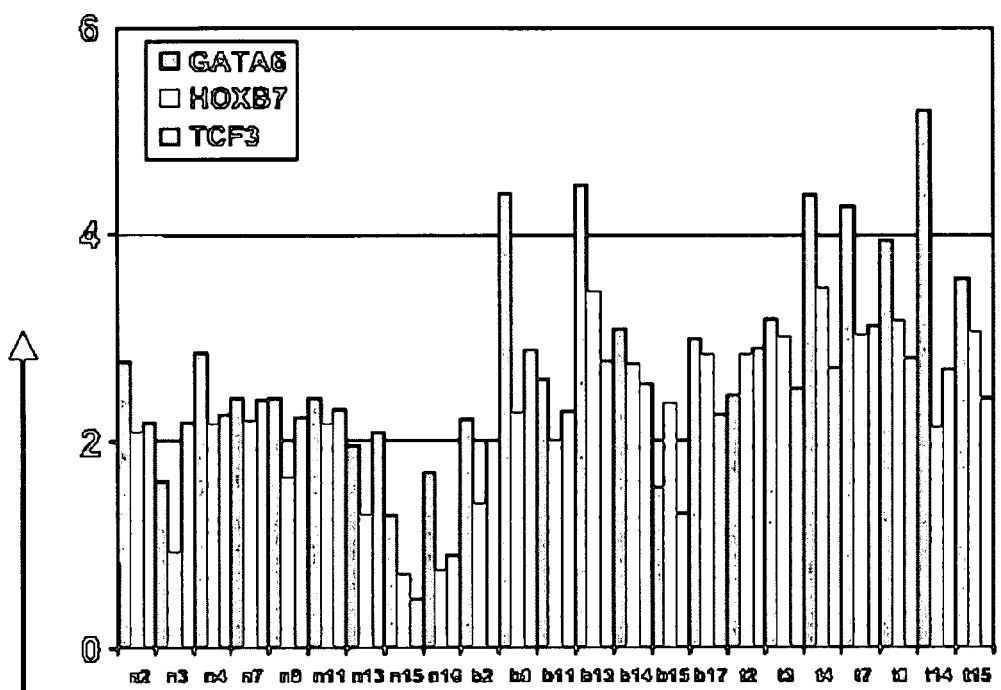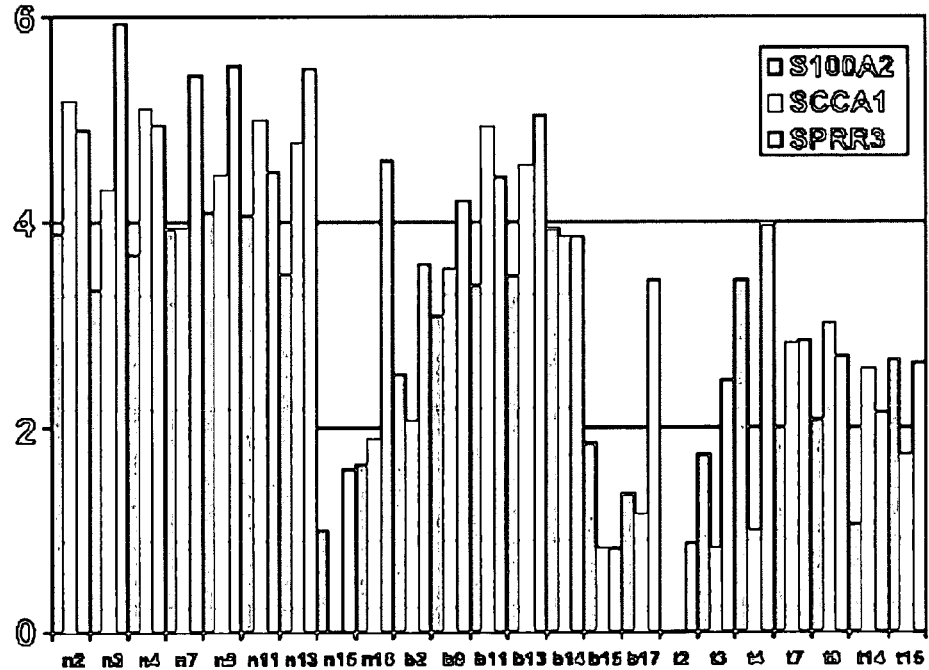
FIGS. 1A & B

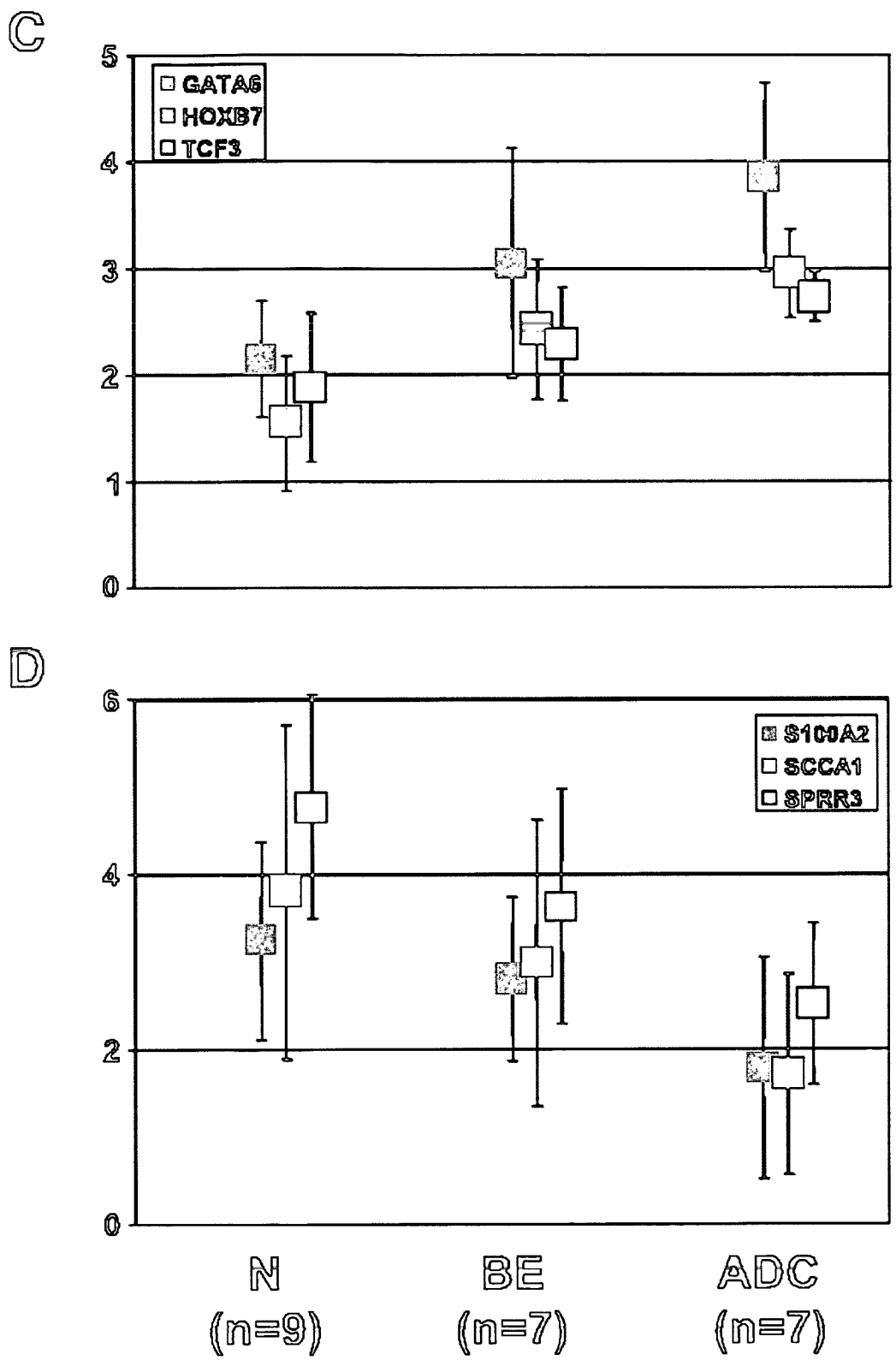
FIGS. 1C & D

METHODS AND KITS FOR MONITORING BARRETT'S METAPLASIA

CROSS-REFERENCE TO RELATED APPLICATIONS

This application claims the benefit of U.S. Provisional Application No. 60/658,424, filed Mar. 2, 2005.

STATEMENT REGARDING FEDERALLY SPONSORED RESEARCH OR DEVELOPMENT

The invention was made with U.S. Government support under Grant No. CA071933, awarded by The National Institutes of Health. The U.S. Government may have certain rights to this invention.

BACKGROUND OF THE INVENTION

Barrett's esophagus is a specialized intestinal metaplasia of normal squamous to columnar epithelium, which is thought to be a premalignant transformation and which is found in 80-100% of esophageal adenocarcinoma of the distal esophagus (1). The etiology of Barrett's esophagus is not well understood, but chronic gastroesophageal reflux is considered to be a major contributing factor (2). The presence of Barrett's esophagus increases the risk of developing adenocarcinoma 40 to 125-fold (3). The incidence of adenocarcinoma has increased 3.5-fold over the past 3 decades, which exceeds that of all other types of cancer (4, 5). Patients with adenocarcinomas of the esophagus present with advanced disease, and 5-year survival is approximately 25% (6). Currently, endoscopic surveillance is the only method of identifying patients with early-stage esophageal cancers arising in Barrett's esophagus.

Identification of biological markers of Barrett's esophagus progression may identify high risk patients for whom endoscopy would be indicated (8). Expressional profiling represents one method of identifying biological markers of Barrett's esophagus (9-12). However, no molecular markers that can be used to identify patients at higher risk for subsequent transformation of Barrett's esophagus to adenocarcinoma have been reported.

There exists a need in the art for new methods of evaluating the risk of progression of Barrett's esophagus to adenocarcinoma.

BRIEF SUMMARY OF THE INVENTION

In one aspect, the present invention provides methods of assessing risk of adenocarcinoma in a mammal with Barrett's esophagus. The method involves measuring the level of expression of at least two markers listed in Table 2 in a sample prepared from Barrett's esophageal cells. The level of expression in Barrett's esophageal cells is compared to that of a reference, a difference in the level of expression of a marker being indicative of increased risk of adenocarcinoma.

In another aspect, the invention provides kits for performing the methods of the invention.

BRIEF DESCRIPTION OF THE DRAWINGS

FIG. 1A-D shows plots of expression levels of markers as a function of sample type.

DETAILED DESCRIPTION OF THE INVENTION

Figure 2:
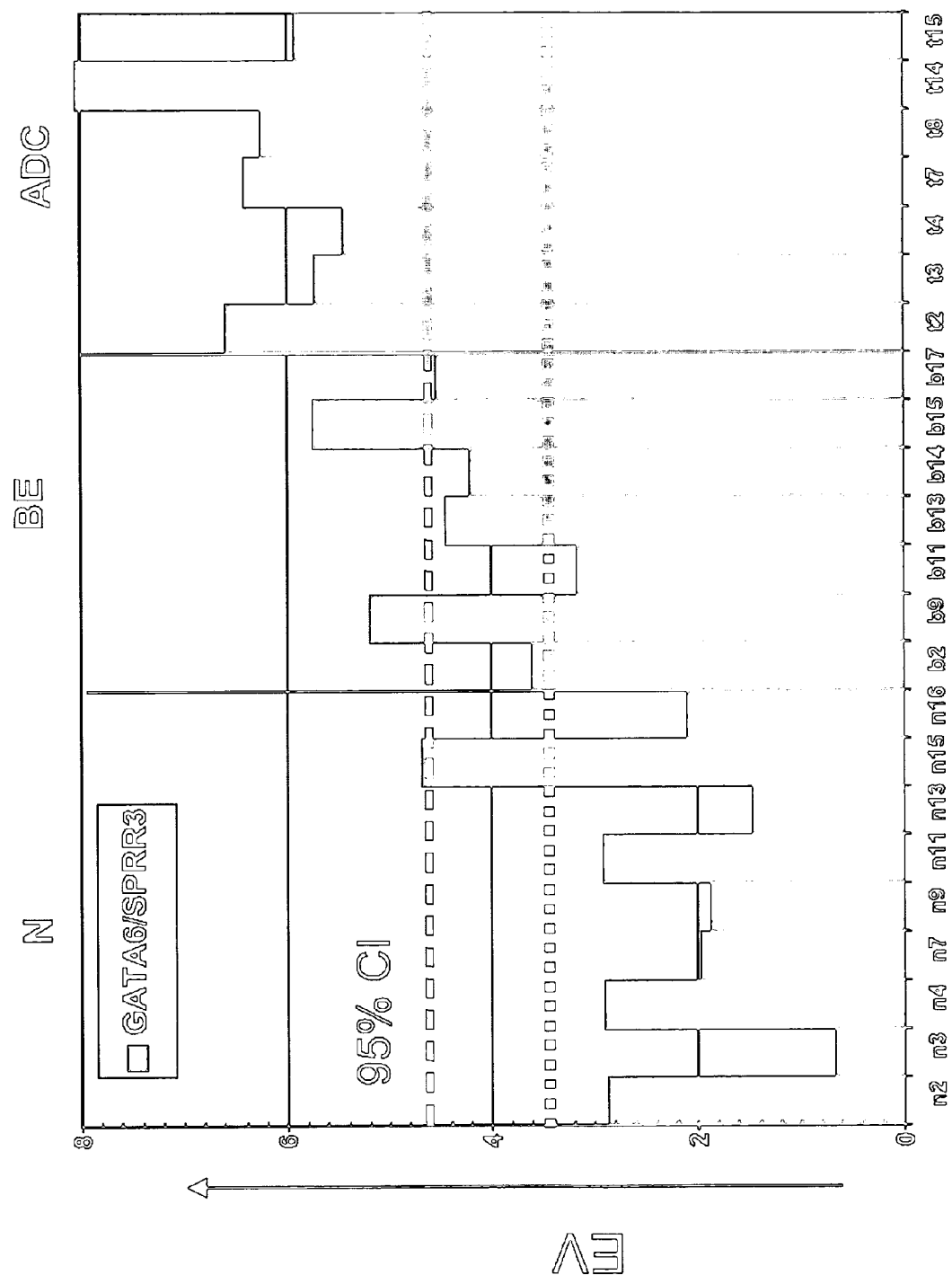
FIG. 2 shows a plot of the ratio of expression levels of two markers as a function of sample type.

The Examples below describe the identification of molecular markers differentially expressed in normal esophageal epithelium, Barrett's esophagus, and esophageal adenocarcinoma. Measuring the level of expression of these markers allows discrimination between normal esophageal epithelium, Barrett's esophagus, and esophageal adenocarcinoma. Quantitation of these markers can be used to identify patients with Barrett's esophagus at increased risk for subsequent progression to adenocarcinoma.

DNA microarrays were used to evaluate differential gene expression patterns in resected esophageal specimens composed of normal esophageal epithelium, Barrett's esophagus, and adenocarcinoma obtained from the same individual patients. Based on this analysis, 96 genes that are differentially expressed in both Barrett's esophagus and adenocarcinoma were identified (Supplemental Table 2).

Of the 96 genes differentially expressed in Barrett's esophagus and adenocarcinoma, 21 genes (Table 2) were identified as being potentially useful for evaluating risk of progression from Barrett's esophagus to esophageal adenocarcinoma. These 21 genes were chosen because the change in expression is in the same direction (i.e., up-regulation or down-regulation) in both Barrett's esophagus and to esophageal adenocarcinoma, and because the change in expression is progressive from Barrett's esophagus to esophageal adenocarcinoma (i.e., the markers are up- or down-regulated to a greater degree in esophageal adenocarcinoma than in Barrett's esophagus). Because the change in expression from Barrett's esophagus to esophageal adenocarcinoma is progressive, is reasonably expected that the markers can be used to monitor progression from Barrett's esophagus to esophageal adenocarcinoma.

Of the 21 genes, six selected genes (GATA6, HOXB7, TCF3, S100A2, SCCA1 and SPRR3) were further evaluated. The level of expression of these genes, as measured by quantitative reverse transcription-PCR (QRT-PCR), discriminated between normal epithelium, Barrett's dysplasia and esophageal adenocarcinomas. It is possible to discriminate between normal epithelium and Barrett's esophagus or esophageal adenocarcinomas using any one of the 21 markers. Analysis of two or more markers permits discrimination Barrett's esophagus and esophageal adenocarcinomas. In the Examples, expression levels of GATA6/SPRR3, HOXB7/SPRR3, and GAT6/HOXB7/SPRR3 were evaluated and found to discriminate between Barrett's esophagus and esophageal adenocarcinomas. Additionally, it is specifically envisioned that any combination of two or more of the 21 markers provided in Table 2 will be useful in the methods of the invention. The markers may be analyzed individually or together in a multiplex.

In the methods of the invention, the level of gene expression was performed by indirectly measuring the mRNA by quantitative PCR, as described in the Examples. It is envisioned that mRNA, or cDNA prepared from mRNA, could be quantified through standard hybridization techniques using an oligonucleotide complementary to at least a portion of the mRNA or cDNA. Alternatively, the level of gene expression could be assayed using antibody detection methods and an antibody specific for an epitope of one of the gene products (i.e., mRNA or protein) of the 21 markers.

In the Examples, gene expression was evaluated by comparing expression levels of the 21 markers in normal esophageal epithelium, cells characteristic of Barrett's esophagus, and esophageal adenocarcinoma using resected esophagus samples. It is envisioned that any sample containing cells characteristic of Barrett's esophagus could be used. For example, such cells may be obtained by an esophageal lavage, or scraping or biopsying a portion of the esophagus during endoscopy.

Marker expression levels in Barrett's esophagus can be evaluated by comparison to a reference. The reference may be normal esophageal epithelium obtained from the same individual, at the same time or at a different time. Alternatively, the reference may be marker expression levels in a sample comprising cells characteristic of Barrett's esophagus obtained from the same individual at a different time, which would permit changes in marker expression levels to be monitored over time. It is also envisioned that comparison of marker expression levels may be made with reference to a normal range established using normal cells from a population of individuals.

Differences in expression levels between Barrett's esophagus and a reference may be evaluated using any suitable statistical test. As one of skill in the art will appreciate, interpretation of results may be evaluated using different P values, depending on importance of minimizing false positives relative to the importance of minimizing false negatives in a particular application.

The methods of the invention may conveniently be performed using a kit. The kit may optionally comprise one or more probes for measuring expression at least one marker of Table 2. A probe may include, for example, a primer pair for performing quantitative PCR, an oligonucleotide that hybridizes to an mRNA or cDNA corresponding to one of the markers of Table 2, or an antibody specific for an epitope of an expression product (i.e., mRNA or protein) of a marker listed in Table 2. The kit may include instructions for performing a method according to the present invention.

EXAMPLES

The following non-limiting Examples are intended to be purely illustrative.

Clinical samples. Samples of normal, Barrett's, and adenocarcinoma were obtained from fresh pathological specimens of patients with known Barrett's esophagus and esophageal adenocarcinoma who had undergone esophagectomy. These specimens were processed by pathology within 15 minutes of resection. Samples representative of the various gross histologic types were obtained from experienced gastrointestinal pathologists. These samples were labeled and snap frozen in liquid nitrogen and stored at −80° C. for future RNA extraction.

Preparation of RNA and hybridizations. RNAs were purified by combination of column chromatography and TRizol (GIBCO BRL, MD) purification, as described previously (15). Preparation of labeled cRNA and hybridization with U133A chips was performed according to the manufacturer's instructions (Affymetrix, Calif.). Data were acquired using MAS 5.0 software (Affymetrix) and exported to MS Excel.

Submission of DNA array data. Data were submitted to the Microarray Analysis and Data Management System (MADAM) database of the University of Chicago, and constructed according to the Minimum Information about a Microarray Experiment (MIAME) recommendations. Data were also submitted to the GEO database (NCBI), with the accession number GSE1420.

Data analysis. Throughout this section, patients are denoted by the letter i=1, . . . 8, genes by the letter j, and tissue type by the letter k=1, 2, 3 (referring to normal (N), Barrett's esophagus (BE), and adenocarcinoma tumor (ADC).

For data normalization, the expression levels of each array were multiplied by $\overline{M}/M$, where M is the median expression of the array, and $\overline{M}$ is the overall median expression level. This resealing makes median expression levels equal across all arrays. For data filtration, genes were excluded based on present (P) or absent (A) calls as defined by MAS 5.0. Genes were excluded if $\Sigma_{i=1}^{8} A_i \geq 3$ for all three tissue types, where $A_i$ indicates whether a transcript is absent ($A_i=1$) or present ($A_i=0$). The genes were further filtered based on signal intensities using ROC analysis as previously described (16, 17). The total number of remaining genes was 8636.

Next, Significance Analysis of Microarrays (SAM) (18) was used to identify genes significantly over- and underexpressed in the three pairwise comparisons of Barrett's/normal, adenocarcinoma/normal, and Barrett's/adenocarcinoma. Significance analysis of microarrays identified genes with statistically significant differences between groups by assigning each gene a score on the basis of the difference in gene expression between two groups (e.g. normal and Barrett's) relative to the adjusted pooled standard deviation of the multiple measurements from both groups. Permutations of the measurements were then used to estimate the false discovery ratio (FDR), the percentage of genes identified by chance. As the cut-off point, a Δ-value was chosen such that the estimated median number of falsely discovered (called) genes was less than or equal to 1, and required at least a 2-fold expression ratio. In contrast to using a cut-off point of a fixed FDR level, this approach resulted in different cut-off Δs and FDR levels for the three comparisons: Barrett's/normal (Δ=1.270, FDR=0.33%), adenocarcinoma/normal, (Δ=1.555, FDR=0.121%) and Barrett's/adenocarcinoma (Δ=0.892, FDR=0.876%). Based on these criteria, 447 genes significantly expressed in adenocarcinoma compared with normal epithelium and 200 genes significantly expressed in Barrett's esophagus compared with normal epithelium were selected. A set of 85 genes was found to have significantly different expression between adenocarcinoma and Barrett's esophagus, of which 45 genes overlapped with genes significantly different in adenocarcinoma versus normal epithelium. Next, expression ratios of all genes between two tissue groups were compared to the reference "same-to-same" distribution in order to identify genes for which the ratios are larger than expected. In a simple case with two normal samples, the "same-to-same" distribution is the distribution of over all genes j (17). This concept was extended to a situation with more than two arrays by considering $$L_j = \log_2 \left[ \left( \frac{N_{j1} \cdot N_{j2} \cdots N_{j,\frac{K}{2}}}{N_{j,\frac{K}{2}+1} \cdot N_{j,\frac{K}{2}+2} \cdots N_{jK}} \right)^{1/(K/2)} \right]$$

where K is an even number of normal samples, and $N_{jk}$ represents the expression level of gene j. For every gene j, we consider the $$C = \binom{K}{K/2}$$

possible ways the samples can be separated into two groups, obtaining C=70 possible combinations for each gene based on the 8 arrays, hybridized with RNA from normal tissues. For each of the 70 distributions quantiles $q_{0.005}$, $q_{0.0025}$, $q_{0.0975}$, $q_{0.995}$, corresponding to nonparametric 95% and 99% confidence limits were computed. Averaging these over the 70 combinations provides cut-off points for where the bulk of the same-to-same log-ratios occur. For each gene j Barrett's/normal and adenocarcinoma/normal ("different-to-same") log-ratio $$L_j = \log_2\left[\left(\frac{T_{j1} \cdot T_{j2} \ldots \cdot T_{jK}}{N_{j1} \cdot N_{j2} \ldots \cdot N_{jK}}\right)^{1/K}\right]$$

was then compared to the reference "same-to-same" distributions, and genes with expression ratios outside the cut-off limits were considered to be differentially expressed. Using the geometric mean rather than the non-standardized ratio allowed direct comparisons of the distributions of the "same-to-same" and "different-to-same" hybridizations, adjusting for the fact that the "different-to-same" ratios are based on K pairs of tumor and normal expression levels, and that the "same-to-same" ratios are based only on K normal expression levels. Thus, $L_j$ can be naturally interpreted as the per-patient log-ratio.

Functional selection and prognosticators analysis. To select functionally significant groups of genes, OntoExpress software was used (19). Functional groups containing at least 3 genes were selected and analyzed using a binomial distribution with a significance level ≦0.05. Combining results of functional and expression-based selections, 214 genes were selected for further study. Two-dimensional hierarchical clustering of these genes was performed based on the estimation of the Euclidian distances by Ward's method using $\log_2 X_{ijk}/\overline{X}_j^{(N)}$, the log-transformed expression levels normalized to the average expression level in the normal tissues, $\overline{X}_j^{(N)}$. Samples T5 and N8 were removed as outliers. For clustering and data presentation, JMP and TreeView software was used as described previously (20).

To define genes that correlate with the progression of Barrett's esophagus to adenocarcinoma, the 96 genes expressed in both Barrett's esophagus and adenocarcinoma were considered. These genes were separated into two groups based on average between-patient expression: the first group contained genes which were up-regulated from normal to Barrett's esophagus and further from Barrett's esophagus to adenocarcinoma, and the second group was defined similarly for down-regulated genes. All other potential patterns were excluded from this analysis. The significance of the difference in expression from normal to Barrett's esophagus and from Barrett's esophagus to adenocarcinoma in each group was evaluated by a one-sided paired t-test using a p-value≦0.05 cut-off (taking into account that up- or down-regulated genes in each group had been pre-selected).

Quantitative reverse-transcription-PCR. cDNA was synthesized using Superscript II® reverse transcriptase (Invitrogen Life Technologies, Carlsbad, Calif., USA) following the manufacturer's instructions. cDNA was diluted 1:10 in sterile nuclease free water (Ambion, Tex.). Quantitative PCR was performed on an ABI 7700 system (Applied Biosystems, Foster City, Calif.) using SYBR Green PCR reagents in a 25 µl reaction mixture containing 2.5 µl 10×SYBR Green PCR buffer, 0.25 µl 10 mM primers, 2 µl dNTP mix, 3 µl 25 mM $MgCl_2$, 0.25 µl AmpErase, 0.125 µl Amplitaq Gold and 2.5 µl of the 1:10 diluted cDNA.

Primers for selected genes were designed based on UniGene reference sequences using PrimerExpress software (Applied Biosystems, Foster City, Calif.). For the internal control we used GAPDH. PCR was performed for 40 cycles at 95° C. for 15 seconds and 60° C. for one minute after initial incubations at 50° C. for 2 minutes and 95° C. for 10 min.

All samples were amplified in triplicate reactions. The expression of each individual gene was calculated based on the difference between amplification of the individual mRNA template and the internal control (GAPDH) mRNA template. These differences were measured by delta ct (dct) values as described in the manufacturer's instructions (Applied Biosystems, Foster City, Calif.). dct values were calculated as ($ct_x$-$ct_{GAPDH}$), where $ct_x$ is the ct value of the specific gene X and $ct_{GAPDH}$ is the amplification of the internal control. Fold induction was calculated as $2^{-dct}$ and therefore was equal to $2^{-(ct_x - ct_{GAPDH})}$ Ratios of gene X relative to gene Y in the same samples was calculated as: $R_{X/Y} = 2^{-(ctX - ctY)}$. These ratios were multiplied by 100,000 to give a range greater than one. Finally, the data was converted to $Log_{10}$ format to present them in linear scale. The final expressional value (EV) was calculated as:

$$EV_{x/y} = Log_{10}[10^5 \times \{2^{-(ctX-ctY)}\}]$$

Discrimination between normal esophageal epithelium, Barrett's metaplasia and adenocarcinomas based on expressional profiling. Genes differentially expressed (either up- or down-regulated) in Barrett's esophagus and adenocarcinoma were selected based on the results of the statistical analysis. Compared with normal esophageal epithelium, 200 genes differentially expressed in Barrett's esophagus tissue and 447 genes differentially expressed in the Barrett's esophagus-associated adenocarcinoma were identified. The comparison of genes differentially expressed in Barrett's esophagus and adenocarcinoma showed that 96 genes were commonly over-expressed in Barrett's esophagus and adenocarcinoma. In adenocarcinoma, 351 genes were found to be differentially expressed that are not differentially expressed in Barrett's esophagus; in Barrett's esophagus, 104 genes were found to be differentially expressed that are not differentially expressed in adenocarcinoma. These non-overlapping genes were used in subsequent selection of significant functional groups using OntoExpress software (Table 1). Genes were also selected by comparison of the "same-to-same" and "different-to-same" hybridizations as described above using 99% confidence intervals based on the non-parametric quantile analysis. Combining both approaches, 214 genes (Supplemental Table 1) were selected for two-dimensional hierarchical clustering to show the actual discrimination between normal samples, Barrett's esophagus, and adenocarcinoma. The data were separated into three expressional clusters: cluster 1 (80 genes) contains the genes up-regulated in adenocarcinoma compared with normal epithelium; cluster 2 (63 genes) contains the genes which are sequentially suppressed in Barrett's esophagus and adenocarcinoma compared with the normal epithelium; cluster 3 (71 genes) contains the genes most drastically suppressed in adenocarcinoma compared with normal epithelium and Barrett's esophagus (data not shown).

Expressional patterns of normal epithelium, Barrett's esophagus and adenocarcinoma include different functional groups of genes. The major functional groups associated with the three major expressional clusters were identified. Cluster 1 was found to contain functional groups of genes associated with immune response, cell-cell signaling and cell-ECM interactions, control of cell cycle/growth/proliferation, and regulation of transcription and receptor activity (see Table 1).

Cluster 2 was also found to include genes involved in regulating cell cycle/proliferation, as well as genes involved in intracellular transport, bile acid transport, and aldehyde and lipid metabolism. Cluster 3 was found to contain functional groups of genes which may be specifically involved in the development of adenocarcinoma, including ectoderm development/epidermal differentiation, cytoskeleton, control of cell shape and cell-to-cell and cell-to-ECM interactions, $Ca^{2+}$ binding and metabolism, and a group of proteases and protease inhibitors. Many of these genes are specifically associated with epidermal differentiation and malignant transformation.

Analysis of genes common to Barrett's and adenocarcinoma. Ninety-six genes were found to be differentially expressed (relative to normal esophageal endothelium) in both Barrett's esophagus and adenocarcinomas (Supplemental Table 2). Of those genes, a subset of 21 genes (Table 2) was chosen as prognostic or diagnostic markers because they are differentially expressed in the same direction (i.e., up- or down-regulated) in both Barrett's esophagus and adenocarcinoma, relative to normal esophageal epithelium, and the changes in expression are progressive from Barrett's esophagus to adenocarcinoma (i.e., expression is up- or down-regulated to a greater degree in adenocarcinoma relative than in Barrett's esophagus).

Analysis of expression by QRT-PCR. Differential expression as determined by DNA array-based analysis was confirmed for select markers within the group of markers shown in Table 2 using QRT-PCR. Briefly, RNA was purified from surgical samples, and QRT-PCR was performed, as described above, for GATA6, HOXB7, TCF3, S100A2, SCCA1 and SPRR3, with GAPDH as the internal control, using primer pairs having the sequences provided in Table 3. The results are shown in FIGS. 1 and 2. With reference to FIG. 1, panel A shows the expressional value (EV) calculated relative to GAPDH for three transcriptional factors (i.e., GATA6, HOXB7 and TCF3) for individual paired patient samples. Patient samples are identified by patient number and sample type, i.e., normal esophageal epithelium (n), Barrett's dysplasia (b), or esophageal adenocarcinoma (t). The results indicate that these genes are up-regulated in the progression from normal to Barrett's esophagus to adenocarcinoma. Panel B shows expressional value (EV) calculated relative to GAPDH for three genes related to keratinocyte differentiation (i.e., S100A2, SCCA1 and SPRR3) for individual paired patient samples. The results indicate that these genes are down-regulated in the progression from normal to Barrett's esophagus to adenocarcinoma. Four samples (n12, n14, nN17 and t17) failed to amplify specific gene products by PCR and were excluded. These data are consistent with the results from the entire set of tissue types in the microarray analysis, as shown in FIGS. 1C and D, which show the corresponding average values, with the standard deviations indicated by the error bars.

To select expressional markers correlated with pre-malignant and malignant changes, p values and regression coefficients were calculated for six single genes and combinations of genes (Table 4). Each single marker can significantly discriminate normal esophageal epithelium from adenocarcinoma. However, only HOXB7 can discriminate normal tissues from Barrett's. None of the tested markers used alone can discriminate Barrett's from adenocarcinomas. However, as can be seen from Table 4, combinations of markers (GATA6/SPRR3, HOXB7/SPRR3 and GATA6+HOXB7/SPRR3) permit discrimination of Barrett's from adenocarcinomas. Additionally, mixed effects analysis of variance (ANOVA) models were used to determine whether there are differences in expression of GATA6/SPRR3, HOXB7/SPRR3 and GATA6+HOXB7/SPRR3 combinations between the three groups, accounting for the presence of intra-subject correlation due to the presence of several subjects with multiple samples. These analyses confirmed that the expression levels of these combination markers are significantly different between normal, Barrett and Tumor tissues types (data not shown). Also, for the combinations listed, the correlation between expression and tumor progression is higher than for either gene alone.

The GATA6/SPRR3 ratio was evaluated as marker of transformation (FIG. 2). As can be seen in FIG. 2, the ratio of GATA6 to SPRR3 progressively increases along the progression from normal epithelium to Barrett's dysplasia to adenocarcinomas. At the 95% confidence interval (dashed line, calculated as the mean of normal epithelium values+1.96 SD), the test has a specificity of 89% (8/9 negatives cases). For Barrett's esophagus, the sensitivity of the test, as measured by the percentage of positive cases, is 28.6% (2/9). For adenocarcinoma, the sensitivity is 100% (7/7). With a cut off level equal to 67% confidence interval (mean+1 SD), the specificity of the test is also equal to 89%, the sensitivity for Barrett's esophagus is 86% (6/7), and the sensitivity for adenocarcinoma is 100% (7/7).

Each reference cited herein is incorporated by reference in its entirety.

Table 1. Functional groups of genes selected for Barrett's and adenocarcinomas.

TABLE 1

Selected functional groups for Barrett's and adenocarcinomas

| BARRETT | | Adenocarcinomas | | | |
|---|---|---|---|---|---|
| | | GO Biological process | | GO Molecular function | |
| GO ID | Function name | GO ID | Function name | GO ID | Function name |
| | GO Biological process | GO:0001558 | regulation of cell growth | GO:0003700 | transcription factor activity |
| GO:0000074 | regulation of cell cycle | GO:0006081 | aldehyde metabolism | GO:0003821 | class II major histocompatibility complex |
| GO:0001501 | skeletal development | GO:0006355 | regulation of transcription, DNA-dependent | GO:0004029 | aldehyde dehydrogenase (NAD) activity |
| GO:0006812 | cation transport | GO:0006461 | protein complex assembly | | |
| GO:0006915 | apoptosis | GO:0006629 | lipid metabolism | GO:0004263 | chymotrypsin activity |
| GO:0006935 | chemotaxis | GO:0006886 | intracellular protein transport | GO:0004295 | trypsin activity |
| GO:0006955 | immune response | GO:0006899 | nonselective vesicle transport | GO:0004601 | peroxidase activity |
| GO:0007160 | cell-matrix adhesion | GO:0006944 | membrane fusion | GO:0004867 | serine protease inhibitor activity |
| GO:0007166 | cell surface receptor linked signal transduction | GO:0006979 | response to oxidative stress | GO:0004930 | G-protein coupled receptor activity |
| GO:0007229 | integrin-mediated signaling pathway | GO:0007048 | oncogenesis | GO:0005152 | interleukin-1 receptor antagonist activity |
| | | GO:0007398 | ectoderm development | | |

TABLE 1-continued

Selected functional groups for Barrett's and adenocarcinomas

| BARRETT | | Adenocarcinomas | | | |
|---|---|---|---|---|---|
| | | GO Biological process | | GO Molecular function | |
| GO ID | Function name | GO ID | Function name | GO ID | Function name |
| GO:0007267 | cell-cell signaling | GO:0007417 | central nervous system development | GO:0005198 | structural molecule activity |
| GO:0008151 | cell growth and/or maintenance | GO:0008284 | positive regulation of cell proliferation | GO:0005200 | structural constituent of cytoskeleton |
| GO:0008152 | metabolism | | | GO:0005509 | calcium ion binding |
| GO:0009653 | morphogenesis | GO:0008544 | epidermal differentiation | GO:0005524 | ATP binding |
| | GO Molecular function | GO:0016049 | cell growth | GO:0005525 | GTP binding |
| GO: 0004716 | receptor signaling protein tyrosine kinase | GO:0019883 | antigen presentation, endogenous antigen | GO:0008237 | metallopeptidase activity |
| | | | | GO:0016301 | kinase activity |
| GO:0004872 | receptor activity | GO:0019885 | antigen processing via MHC I | GO:0016853 | isomerase activity |
| GO:0004895 | cell adhesion receptor activity | GO:0045786 | negative regulation of cell cycle | GO:0030106 | MHC class I receptor activity |
| GO:0008201 | heparin binding | null | cell shape and cell size control | GO:0045012 | MHC class II receptor activity |
| | | GO:0006470 | protein amino acid dephosphorylation | GO:0004033 | aldo-keto reductase activity |
| | | | | GO:0005488 | binding |
| | | GO:0006805 | xenobiotic metabolism | GO:0008014 | calcium-dependent cell adhesion |
| | | GO:0006810 | transport | GO:0015125 | bile acid transporter activity |
| | | GO:0006955 | immune response | GO:0017017 | MAP kinase phosphatase activity |
| | | GO:0007155 | cell adhesion | GO:0047115 | trans-1,2-dihydrobenzene-1,2-diol dehydrogenase |
| | | GO:0007156 | homophilic cell adhesion | | |
| | | GO:0007267 | cell-cell signaling | | |

Table 2. Genes progressively up- or down-regulated with the development of adenocarcinoma from Barrett's esophagus.

TABLE 2

Genes with progressive changes of expression in Barretts and adenocarcinomas

| id | symbol | name | Ratio (B/N) | Ratio (T/N) |
|---|---|---|---|---|
| | | up-regulated genes | | |
| 201301_s_at | ANXA4 | ANNEXIN A4 | 2.28 | 3.13 |
| 201954_at | ARPC1B | ACTIN-RELATED PROTEIN 2/3 COMPLEX, SUBUNIT 1B | 3.20 | 5.42 |
| 214439_x_at | BIN1 | BRIDGING INTEGRATOR 1 | 2.23 | 3.26 |
| 202901_x_at | CTSS | CATHEPSIN S | 3.08 | 5.26 |
| 210002_at | GATA6 | GATA-BINDING PROTEIN 6 | 6.27 | 10.77 |
| 221875_x_at | HLA-F | MAJOR HISTOCOMPATIBILITY COMPLEX, CLASS I, F | 2.28 | 3.35 |
| 204806_x_at | HLA-F | MAJOR HISTOCOMPATIBILITY COMPLEX, CLASS I, F | 2.17 | 3.20 |
| 204779_s_at | HOXB7 | HOMEO BOX B7 | 3.56 | 5.82 |
| 216973_s_at | HOXB7 | HOMEO BOX B7 | 2.71 | 4.42 |
| 201422_at | IFI30 | INTERFERON-GAMMA-INDUCIBLE PROTEIN 30 | 2.23 | 4.11 |
| 212110_at | KIAA0062 | SLC39A14: solute carrier family 39 (zinc transporter), member 14 | 5.26 | 7.86 |
| 203943_at | KIF3B | KINESIN FAMILY MEMBER 3B | 2.27 | 3.43 |
| 218376_s_at | NICAL | NEDD9 interacting protein with calponin homology and LIM domains | 2.03 | 3.12 |
| 219622_at | RAB20 | RAB20, member RAS oncogene family | 2.90 | 4.66 |
| 201206_s_at | RRBP1 | RIBOSOME BINDING PROTEIN 1 | 4.02 | 5.80 |
| 201204_s_at | RRBP1 | RIBOSOME BINDING PROTEIN 1 | 2.46 | 3.34 |
| 213811_x_at | TCF3 | TRANSCRIPTION FACTOR 3 | 2.84 | 4.45 |
| 208998_at | UCP2 | UNCOUPLING PROTEIN 2 | 3.52 | 6.57 |
| | | down-regulated genes | | |
| 210020_x_at | CALML3 | CALMODULIN-LIKE 3 | 0.40 | 0.11 |
| 203585_at | ZNF185 | ZINC FINGER PROTEIN 185 | 0.46 | 0.17 |
| 213005_s_at | KANK | KIDNEY ANKYRIN REPEAT-CONTAINING PROTEIN | 0.49 | 0.24 |
| 211734_s_at | FCER1A | Fc FRAGMENT OF IgE, HIGH AFFINITY I, RECEPTOR FOR, ALPHA SUBUNIT | 0.25 | 0.14 |
| 201848_s_at | BNIP3 | BCL2/ADENOVIRUS E1B 19-KD PROTEIN-INTERACTING PROTEIN 3 | 0.43 | 0.26 |
| 219100_at | FLJ22559 | hypothetical protein | 0.48 | 0.29 |

TABLE 3

Primers for detection of genes progressively changing in Barrett's associated adenocarcinomas.

| Gene | forward primer | reverse primer |
|---|---|---|
| gapdh | TGCACCACCAACTGCTTAGC SEQ ID NO: 1 | GGCATGGACTGTGGTCATGAG SEQ ID NO: 2 |
| gata6 | AGCGCGTGCCTTCATCAC SEQ ID NO: 3 | GCAAGTGGTCTGGGCACC SEQ ID NO: 4 |
| hoxb7 | GGATCTACCCCTGGATGCG SEQ ID NO: 5 | GTCTTTCCGTGAGGCAGAGC SEQ ID NO: 6 |
| s100a2 | CTGTCTCTGCCACCTGGTCT SEQ ID NO: 7 | CTCAAAGGCATCAACAGTCCT SEQ ID NO: 8 |
| serpinb3 (SCCA1) | TTCATGTTCGACCTGTTCCA SEQ ID NO: 9 | GCAGCTTTTCCTGTGGTGTT SEQ ID NO: 10 |
| sprr3 | ATCCCTGAGCAGCTGAAGAC SEQ ID NO: 11 | CTGCTGTTGAAGCTGAGGTG SEQ ID NO: 12 |
| tcf3 | GTGACATCAACGAGGCCTTT SEQ ID NO: 13 | CTGCTTTGGGATTCAGGTTC SEQ ID NO: 14 |

TABLE 4 p values and Pearson's correlation coefficients.

| | p values | | | R values |
|---|---|---|---|---|
| Gene symbol | N-ADENOCARCINOMA | N-BE | BE-ADENOCARCINOMA | |
| GATA6 | 0.0014 | 0.0797 | 0.1510 | 0.6909 |
| HOXB7 | 0.0001 | 0.0183 | 0.1045 | 0.7657 |
| TCF3 | 0.0063 | 0.2048 | 0.0769 | 0.5797 |
| S100A2 | 0.0332 | 0.4123 | 0.1131 | −0.4752 |
| SCCA1 | 0.0171 | 0.3794 | 0.1184 | −0.4551 |
| SPRR3 | 0.0011 | 0.1116 | 0.1014 | −0.6177 |
| GATA6/SPRR3 | 1.4662E−06 | 0.0012 | 0.0013 | 0.8732 |
| HOXB7/SPRR3 | 4.0369E−06 | 0.0092 | 0.0211 | 0.8176 |
| GATA6 + HOXB7/SPRR3 | 1.6406E−06 | 0.0028 | 0.0034 | 0.8628 |

SUPPLEMENTAL TABLE 1

| 1 Probe set id | 2 Gene symbol | 3 Expressional cluster number | 4 Gene number in FIG. 2 | 5 Expression in Barrett's relative to the normal epithelium [Log2 R (B/N)] | 6 Expression in adenocarcinoma relative to normal epithelium [Log2 R (T/N)] |
|---|---|---|---|---|---|
| 205927_s_at | CTSE | 1 | 1 | 4.55 | 4.83 |
| 219580_s_at | TMC5 | 1 | 2 | 4.21 | 5.46 |
| 210143_at | ANXA10 | 1 | 3 | 5.38 | 4.62 |
| 203824_at | TM4SF3 | 1 | 4 | 2.73 | 3.07 |
| 203559_s_at | ABP1 | 1 | 5 | 3.28 | 3.64 |
| 208161_s_at | ABCC3 | 1 | 6 | 2.43 | 2.70 |
| 204714_s_at | F5 | 1 | 7 | 2.43 | 3.27 |
| 209301_at | CA2 | 1 | 8 | 2.56 | 1.94 |
| 219682_s_at | TBX3 | 1 | 9 | 2.93 | 1.99 |
| 64408_s_at | CLN6 | 1 | 10 | 3.03 | 2.82 |
| 201666_at | TIMP1 | 1 | 11 | 1.49 | 2.04 |
| 220974_x_at | BA108L7.2 | 1 | 12 | 1.34 | 1.34 |
| 219327_s_at | GPRC5C | 1 | 13 | 1.14 | 2.05 |
| 210095_s_at | IGFBP3 | 1 | 14 | 1.55 | 2.57 |
| 219956_at | GALNT6 | 1 | 15 | 2.77 | 2.27 |
| 202910_s_at | CD97 | 1 | 16 | 1.57 | 2.08 |
| 209774_x_at | CXCL2 | 1 | 17 | 1.48 | 1.65 |
| 207522_s_at | ATP2A3 | 1 | 18 | 2.44 | 1.43 |
| 202267_at | LAMC2 | 1 | 19 | 2.11 | 3.01 |
| 210314_x_at | TNFSF13 | 1 | 20 | 2.42 | 3.18 |
| 219795_at | SLC6A14 | 1 | 21 | 3.03 | 3.49 |
| 202625_at | LYN | 1 | 22 | 2.09 | 2.40 |
| 203058_s_at | PAPSS2 | 1 | 23 | 1.19 | 1.43 |
| 210754_s_at | LYN | 1 | 24 | 1.56 | 1.54 |
| 222303_at | ETS2 | 1 | 25 | 1.74 | 0.96 |
| 220322_at | IL1F9 | 1 | 26 | 1.93 | 0.07 |
| 205668_at | LY75 | 1 | 27 | 1.16 | 1.80 |

SUPPLEMENTAL TABLE 1-continued

| 1 Probe set id | 2 Gene symbol | 3 Expressional cluster number | 4 Gene number in FIG. 2 | 5 Expression in Barrett's relative to the normal epithelium [Log2 R (B/N)] | 6 Expression in adenocarcinoma relative to normal epithelium [Log2 R (T/N)] |
|---|---|---|---|---|---|
| 204363_at | F3 | 1 | 28 | 1.11 | 0.03 |
| 203510_at | MET | 1 | 29 | 2.39 | 3.57 |
| 214235_at | CYP3A5 | 1 | 30 | 2.08 | 2.59 |
| 202820_at | AHR | 1 | 31 | 1.86 | 2.59 |
| 210664_s_at | TFPI | 1 | 32 | 1.17 | 1.33 |
| 205289_at | BMP2 | 1 | 33 | 1.62 | 2.05 |
| 201656_at | ITGA6 | 1 | 34 | 1.79 | 1.51 |
| 215177_s_at | ITGA6 | 1 | 35 | 1.40 | 1.02 |
| 221059_s_at | CHST6 | 1 | 36 | 2.43 | 3.02 |
| 205067_at | IL1B | 1 | 37 | 2.42 | 0.84 |
| 210845_s_at | PLAUR | 1 | 38 | 2.15 | 2.51 |
| 211924_s_at | PLAUR | 1 | 39 | 1.99 | 2.27 |
| 206467_x_at | TNFRSF6B | 1 | 40 | 1.83 | 2.44 |
| 39402_at | IL1B | 1 | 41 | 2.84 | 1.04 |
| 209417_s_at | IFI35 | 1 | 42 | 1.28 | 2.04 |
| 201596_x_at | KRT18 | 1 | 43 | 1.62 | 1.83 |
| 204017_at | KDELR3 | 1 | 44 | 1.98 | 2.32 |
| 204989_s_at | ITGB4 | 1 | 45 | 1.18 | 1.16 |
| 207265_s_at | KDELR3 | 1 | 46 | 1.34 | 1.41 |
| 202831_at | GPX2 | 1 | 47 | 1.31 | 1.84 |
| 201189_s_at | ITPR3 | 1 | 48 | 1.36 | 1.71 |
| 202668_at | EFNB2 | 1 | 49 | 1.68 | 1.84 |
| 212282_at | MAC30 | 1 | 50 | 1.34 | 2.66 |
| 212281_s_at | MAC30 | 1 | 51 | 1.41 | 2.67 |
| 212279_at | MAC30 | 1 | 52 | 1.00 | 2.19 |
| 208829_at | TAPBP | 1 | 53 | 0.89 | 1.69 |
| 211529_x_at | HLA-G | 1 | 54 | 0.85 | 1.35 |
| 211911_x_at | HLA-B | 1 | 55 | 0.93 | 1.34 |
| 208729_x_at | HLA-B | 1 | 56 | 0.78 | 1.18 |
| 214459_x_at | HLA-C | 1 | 57 | 0.86 | 1.23 |
| 203857_s_at | PDIR | 1 | 58 | 0.89 | 1.09 |
| 211528_x_at | HLA-G | 1 | 59 | 0.81 | 1.24 |
| 202737_s_at | LSM4 | 1 | 60 | 0.53 | 1.38 |
| 201063_at | RCN1 | 1 | 61 | 0.75 | 1.82 |
| 209762_x_at | SP110 | 1 | 62 | 0.63 | 1.31 |
| 205205_at | RELB | 1 | 63 | 0.87 | 1.16 |
| 213258_at | TFPI | 1 | 64 | 0.99 | 1.19 |
| 210927_x_at | JTB | 1 | 65 | 0.46 | 1.14 |
| 218355_at | KIF4A | 1 | 66 | 1.04 | 1.85 |
| 211048_s_at | ERP70 | 1 | 67 | 0.86 | 1.62 |
| 200699_at | KDELR2 | 1 | 68 | 0.94 | 1.69 |
| 212761_at | TCF7L2 | 1 | 69 | 0.77 | 1.24 |
| 201329_s_at | ETS2 | 1 | 70 | 1.01 | 0.17 |
| 200037_s_at | CBX3 | 1 | 71 | 0.34 | 1.47 |
| 211208_s_at | CASK | 1 | 72 | 0.65 | 1.33 |
| 210052_s_at | TPX2 | 1 | 73 | 0.64 | 1.55 |
| 204641_at | NEK2 | 1 | 74 | 0.68 | 1.95 |
| 204670_x_at | HLA-DRB3 | 1 | 75 | 0.63 | 1.76 |
| 209312_x_at | HLA-DRB3 | 1 | 76 | 0.77 | 1.80 |
| 208306_x_at | HLA-DRB3 | 1 | 77 | 0.78 | 1.83 |
| 215193_x_at | HLA-DRB3 | 1 | 78 | 0.88 | 1.85 |
| 210982_s_at | HLA-DRA | 1 | 79 | 0.73 | 1.53 |
| 208894_at | HLA-DRA | 1 | 80 | 0.53 | 1.27 |
| 211126_s_at | CSRP2 | 2 | 81 | −0.77 | −1.84 |
| 207030_s_at | CSRP2 | 2 | 82 | −0.80 | −1.63 |
| 203659_s_at | RFP2 | 2 | 83 | −0.81 | −1.26 |
| 221960_s_at | RAB2 | 2 | 84 | −0.71 | −1.53 |
| 202582_s_at | RANBP9 | 2 | 85 | −0.70 | −1.61 |
| 209882_at | RIT1 | 2 | 86 | −0.85 | −1.85 |
| 201454_s_at | NPEPPS | 2 | 87 | −0.71 | −1.55 |
| 204119_s_at | ADK | 2 | 88 | −0.75 | −1.59 |
| 208771_s_at | LTA4H | 2 | 89 | −0.51 | −1.40 |
| 200606_at | DSP | 2 | 90 | −0.32 | −1.66 |
| 213572_s_at | SERPINB1 | 2 | 91 | −0.39 | −2.30 |
| 212268_at | SERPINB1 | 2 | 92 | −0.38 | −1.63 |
| 202814_s_at | HIS1 | 2 | 93 | −0.46 | −1.27 |
| 200697_at | HK1 | 2 | 94 | −0.54 | −1.47 |
| 208384_s_at | MID2 | 2 | 95 | −0.66 | −1.47 |
| 201192_s_at | PITPN | 2 | 96 | −0.60 | −1.54 |
| 203081_at | CTNNBIP1 | 2 | 97 | −0.58 | −1.67 |
| 201161_s_at | CSDA | 2 | 98 | −0.54 | −1.57 |

SUPPLEMENTAL TABLE 1-continued

| 1 Probe set id | 2 Gene symbol | 3 Expressional cluster number | 4 Gene number in FIG. 2 | 5 Expression in Barrett's relative to the normal epithelium [Log2 R (B/N)] | 6 Expression in adenocarcinoma relative to normal epithelium [Log2 R (T/N)] |
|---|---|---|---|---|---|
| 211749_s_at | VAMP3 | 2 | 99 | −0.39 | −1.23 |
| 209157_at | DNAJA2 | 2 | 100 | −0.60 | −1.33 |
| 208951_at | ALDH7A1 | 2 | 101 | −0.71 | −1.40 |
| 208950_s_at | ALDH7A1 | 2 | 102 | −0.80 | −1.47 |
| 201337_s_at | VAMP3 | 2 | 103 | −0.62 | −1.70 |
| 201612_at | ALDH9A1 | 2 | 104 | −0.85 | −1.56 |
| 41644_at | SASH1 | 2 | 105 | −0.65 | −2.01 |
| 213236_at | SASH1 | 2 | 106 | −1.08 | −2.48 |
| 210094_s_at | PARD3 | 2 | 107 | −0.44 | −1.18 |
| 221526_x_at | PARD3 | 2 | 108 | −0.63 | −1.18 |
| 214040_s_at | GSN | 2 | 109 | −0.93 | −2.37 |
| 202054_s_at | ALDH3A2 | 2 | 110 | −1.05 | −1.70 |
| 202053_s_at | ALDH3A2 | 2 | 111 | −1.02 | −2.19 |
| 209466_x_at | PTN | 2 | 112 | −1.43 | −2.06 |
| 201041_s_at | DUSP1 | 2 | 113 | 0.22 | −1.11 |
| 201044_x_at | DUSP1 | 2 | 114 | −0.11 | −1.59 |
| 202139_at | AKR7A2 | 2 | 115 | −0.60 | −1.20 |
| 209372_x_at | TUBB | 2 | 116 | −0.86 | −1.77 |
| 215813_s_at | PTGS1 | 2 | 117 | −0.42 | −1.68 |
| 210186_s_at | FKBP1A | 2 | 118 | −0.74 | −1.24 |
| 200678_x_at | GRN | 2 | 119 | −0.92 | −1.46 |
| 216041_x_at | GRN | 2 | 120 | −0.96 | −1.58 |
| 204246_s_at | DCTN3 | 2 | 121 | −0.73 | −1.63 |
| 200886_s_at | PGAM1 | 2 | 122 | −0.45 | −1.62 |
| 204029_at | CELSR2 | 2 | 123 | −0.75 | −2.04 |
| 36499_at | CELSR2 | 2 | 124 | −0.68 | −1.97 |
| 203586_s_at | ARF4L | 2 | 125 | −0.44 | −2.37 |
| 213848_at | DUSP7 | 2 | 126 | −0.28 | −2.13 |
| 200844_s_at | PRDX6 | 2 | 127 | −0.86 | −1.39 |
| 208751_at | NAPA | 2 | 128 | −0.73 | −1.20 |
| 202807_s_at | TOM1 | 2 | 129 | −0.73 | −1.39 |
| 214182_at | ARF6 | 2 | 130 | −0.74 | −1.68 |
| 209193_at | PIM1 | 2 | 131 | −0.96 | −1.95 |
| 205172_x_at | CLTB | 2 | 132 | −0.65 | −1.78 |
| 211043_s_at | CLTB | 2 | 133 | −0.44 | −1.95 |
| 206284_x_at | CLTB | 2 | 134 | −0.65 | −1.95 |
| 200863_s_at | RAB11A | 2 | 135 | −0.51 | −1.58 |
| 200752_s_at | CAPN1 | 2 | 136 | −0.79 | −1.65 |
| 204341_at | TRIM16 | 2 | 137 | −0.82 | −2.50 |
| 204151_x_at | AKR1C1 | 2 | 138 | 0.44 | −0.96 |
| 211653_x_at | AKR1C2 | 2 | 139 | 0.37 | −1.32 |
| 209699_x_at | AKR1C2 | 2 | 140 | 0.47 | −1.03 |
| 216594_x_at | AKR1C1 | 2 | 141 | 0.40 | −1.00 |
| 205403_at | IL1R2 | 2 | 142 | 1.24 | 0.13 |
| 206561_s_at | AKR1B10 | 2 | 143 | 0.58 | −1.07 |
| 205549_at | PCP4 | 3 | 144 | −1.55 | −2.80 |
| 218559_s_at | MAFB | 3 | 145 | −0.99 | −2.39 |
| 204379_s_at | FGFR3 | 3 | 146 | −0.86 | −2.28 |
| 205286_at | TFAP2C | 3 | 147 | −0.62 | −2.58 |
| 203074_at | ANXA8 | 3 | 148 | −0.89 | −4.35 |
| 203407_at | PPL | 3 | 149 | −0.74 | −3.93 |
| 202504_at | TRIM29 | 3 | 150 | −0.65 | −3.94 |
| 204942_s_at | ALDH3B2 | 3 | 151 | −1.33 | −5.08 |
| 202345_s_at | FABP5 | 3 | 152 | −0.24 | −2.58 |
| 201012_at | ANXA1 | 3 | 153 | −0.22 | −2.63 |
| 212657_s_at | IL1RN | 3 | 154 | −0.43 | −3.01 |
| 218677_at | S100A14 | 3 | 155 | −0.39 | −2.56 |
| 201324_at | EMP1 | 3 | 156 | −0.56 | −2.97 |
| 201325_s_at | EMP1 | 3 | 157 | −0.61 | −3.85 |
| 219764_at | FZD10 | 3 | 158 | −0.50 | −2.69 |
| 209191_at | TUBB-5 | 3 | 159 | −0.77 | −2.28 |
| 201348_at | GPX3 | 3 | 160 | −0.84 | −2.71 |
| 205349_at | GNA15 | 3 | 161 | −0.82 | −2.96 |
| 209587_at | PITX1 | 3 | 162 | −0.94 | −3.92 |
| 213279_at | DHRS1 | 3 | 163 | −1.28 | −3.02 |
| 205863_at | S100A12 | 3 | 164 | −0.59 | −3.15 |
| 38158_at | ESPL1 | 3 | 165 | −1.82 | −2.87 |
| 205470_s_at | KLK11 | 3 | 166 | −0.95 | −3.79 |
| 217315_s_at | KLK13 | 3 | 167 | −0.97 | −4.60 |
| 205783_at | KLK13 | 3 | 168 | −1.41 | −4.41 |
| 216243_s_at | IL1RN | 3 | 169 | −1.12 | −4.53 |

SUPPLEMENTAL TABLE 1-continued

| 1<br>Probe set id | 2<br>Gene symbol | 3<br>Expressional cluster number | 4<br>Gene number in FIG. 2 | 5<br>Expression in Barrett's relative to the normal epithelium [Log2 R (B/N)] | 6<br>Expression in adenocarcinoma relative to normal epithelium [Log2 R (T/N)] |
|---|---|---|---|---|---|
| 204777_s_at | MAL | 3 | 170 | −0.74 | −5.21 |
| 14599_at | IVL | 3 | 171 | −0.68 | −4.91 |
| 214549_x_at | SPRR1A | 3 | 172 | −0.74 | −4.05 |
| 204751_x_at | DSC2 | 3 | 173 | −0.32 | −2.35 |
| 204469_at | PTPRZ1 | 3 | 174 | −0.03 | −1.61 |
| 206032_at | DSC3 | 3 | 175 | −0.74 | −4.05 |
| 206166_s_at | CLCA2 | 3 | 176 | −0.66 | −4.29 |
| 210372_s_at | TPD52L1 | 3 | 177 | −0.93 | −2.87 |
| 203786_s_at | TPD52L1 | 3 | 178 | −1.11 | −3.28 |
| 213135_at | TIAM1 | 3 | 179 | −0.67 | −3.20 |
| 203797_at | VSNL1 | 3 | 180 | −1.06 | −2.72 |
| 207059_at | PAX9 | 3 | 181 | −1.36 | −3.68 |
| 204284_at | PPP1R3C | 3 | 182 | −0.68 | −3.72 |
| 211726_s_at | FMO2 | 3 | 183 | −1.01 | −2.95 |
| 204614_at | SERPINB2 | 3 | 184 | −0.77 | −4.47 |
| 207602_at | HAT | 3 | 185 | −0.63 | −3.87 |
| 205595_at | DSG3 | 3 | 186 | −0.47 | −3.58 |
| 209719_x_at | SERPINB3 | 3 | 187 | −0.36 | −3.79 |
| 211906_s_at | SERPINB4 | 3 | 188 | −0.31 | −4.07 |
| 205185_at | SPINK5 | 3 | 189 | −0.63 | −3.03 |
| 210413_x_at | SERPINB4 | 3 | 190 | 0.07 | −4.32 |
| 204734_at | KRT15 | 3 | 191 | −0.92 | −7.56 |
| 220431_at | DESC1 | 3 | 192 | −1.00 | −5.02 |
| 220026_at | CLCA4 | 3 | 193 | −0.61 | −5.19 |
| 217528_at | CLCA2 | 3 | 194 | −0.60 | −4.31 |
| 206276_at | E48 | 3 | 195 | −0.63 | −4.18 |
| 209720_s_at | SERPINB3 | 3 | 196 | −0.32 | −3.72 |
| 208539_x_at | SPRR2B | 3 | 197 | −0.56 | −3.89 |
| 213240_s_at | KRT4 | 3 | 198 | −0.03 | −4.73 |
| 213796_at | SPRR1A | 3 | 199 | −0.27 | −3.30 |
| 219554_at | RHCG | 3 | 200 | −0.61 | −6.05 |
| 205014_at | HBP17 | 3 | 201 | −0.28 | −4.24 |
| 203535_at | S100A9 | 3 | 202 | −0.21 | −3.46 |
| 39248_at | AQP3 | 3 | 203 | −0.42 | −3.75 |
| 204268_at | S100A2 | 3 | 204 | −0.16 | −3.42 |
| 202917_s_at | S100A8 | 3 | 205 | 0.00 | −2.48 |
| 213680_at | KRT6B | 3 | 206 | −0.16 | −2.92 |
| 218990_s_at | SPRR3 | 3 | 207 | −0.07 | −3.18 |
| 207935_s_at | KRT13 | 3 | 208 | −0.19 | −3.89 |
| 209126_x_at | KRT6B | 3 | 209 | −0.18 | −3.52 |
| 201820_at | KRT5 | 3 | 210 | −0.29 | −3.89 |
| 209125_at | KRT6A | 3 | 211 | −0.24 | −3.32 |
| 205064_at | SPRR1B | 3 | 212 | −0.23 | −3.25 |
| 209351_at | KRT14 | 3 | 213 | 0.81 | −2.17 |
| 220664_at | SPRR2C | 3 | 214 | −0.38 | −4.25 |

SUPPLEMENTAL TABLE 2

| Probe set ID | Gene name | Gene symbol | Log2 R (B/N) | Log2 R (T/N) |
|---|---|---|---|---|
| 204272_at | galectin 4 | LGALS4 | 4.90 | 4.83 |
| 211429_s_at | *Homo sapiens* PRO2275 mRNA | unknown | 4.26 | 4.70 |
| 201839_s_at | tumor-associated calcium signal transducer 1 | TACSTD1 | 3.27 | 3.76 |
| 209008_x_at | keratin 8 | KRT8 | 2.88 | 3.00 |
| 209173_at | anterior gradient 2 homolog (*Xenopus laevis*) | AGR2 | 2.87 | 3.25 |
| 213059_at | old astrocyte specifically induced substance | OASIS | 2.76 | 2.97 |
| 212444_at | retinoic acid induced 3 | RAI3 | 2.68 | 2.92 |
| 213036_x_at | ATPase, Ca++ transporting, ubiquitous | ATP2A3 | 2.67 | 1.89 |
| 210002_at | GATA binding protein 6 | GATA6 | 2.65 | 3.43 |
| 212314_at | KIAA0746 protein | KIAA0746 | 2.58 | 3.03 |
| 200644_at | MARCKS-like protein | MLP | 2.52 | 3.00 |
| 212110_at | KIAA0062 protein | KIAA0062 | 2.40 | 2.98 |
| 205632_s_at | phosphatidylinositol-4-phosphate 5-kinase, type I, beta | PIP5K1B | 2.32 | 2.52 |
| 209453_at | solute carrier family 9 | SLC9A1 | 2.08 | 1.57 |
| 212311_at | KIAA0746 protein | KIAA0746 | 2.05 | 2.31 |
| 221766_s_at | chromosome 6 open reading frame 37 | C6orf37 | 2.01 | 2.37 |

SUPPLEMENTAL TABLE 2-continued

| Probe set ID | Gene name | Gene symbol | Log2 R (B/N) | Log2 R (T/N) |
|---|---|---|---|---|
| 201206_s_at | ribosome binding protein 1 homolog 180 kDa (dog) | RRBP1 | 2.01 | 2.54 |
| 217989_at | retinal short-chain dehydrogenase/reductase 2 | RETSDR2 | 1.97 | 2.23 |
| 208891_at | dual specificity phosphatase 6 | DUSP6 | 1.96 | 1.49 |
| 212143_s_at | insulin-like growth factor binding protein 3 | IGFBP3 | 1.89 | 2.51 |
| 220532_s_at | LR8 protein | LR8 | 1.88 | 2.49 |
| 218113_at | transmembrane protein 2 | TMEM2 | 1.86 | 1.92 |
| 204779_s_at | homeo box B7 | HOXB7 | 1.83 | 2.54 |
| 208998_at | uncoupling protein 2 | UCP2 | 1.81 | 2.72 |
| 210264_at | G protein-coupled receptor 35 | GPR35 | 1.70 | 1.91 |
| 201954_at | actin related protein 2/3 complex, subunit 1B, 41 kDa | ARPC1B | 1.68 | 2.44 |
| 202901_x_at | cathepsin S | CTSS | 1.62 | 2.40 |
| 219622_at | RAB20, member RAS oncogene family | RAB20 | 1.53 | 2.22 |
| 213811_x_at | transcription factor 3 | TCF3 | 1.50 | 2.15 |
| 200972_at | tetraspan 3 | TSPAN-3 | 1.49 | 1.50 |
| 218368_s_at | TNF receptor superfamily, member 12A | TNFRSF12A | 1.49 | 1.41 |
| 203028_s_at | cytochrome b-245, alpha polypeptide | CYBA | 1.47 | 2.05 |
| 208892_at | dual specificity phosphatase 6 | DUSP6 | 1.47 | 1.20 |
| 216973_s_at | homeo box B7 | HOXB7 | 1.44 | 2.14 |
| 212552_at | hippocalcin-like 1 | HPCAL1 | 1.42 | 1.68 |
| 209270_at | laminin, beta 3 | LAMB3 | 1.37 | 1.39 |
| 201204_s_at | ribosome binding protein 1 homolog | RRBP1 | 1.30 | 1.74 |
| 202180_s_at | major vault protein | MVP | 1.30 | 1.48 |
| 201579_at | FAT tumor suppressor homolog 1 | FAT | 1.28 | 1.16 |
| 202369_s_at | translocation associated membrane protein 2 | TRAM2 | 1.20 | 1.12 |
| 211799_x_at | major histocompatibility complex, class I, C | HLA-C | 1.19 | 1.40 |
| 201301_s_at | annexin A4 | ANXA4 | 1.19 | 1.65 |
| 221875_x_at | major histocompatibility complex, class I, F | HLA-F | 1.19 | 1.74 |
| 203943_at | kinesin family member 3B | KIF3B | 1.18 | 1.78 |
| 200599_s_at | tumor rejection antigen (gp96) 1 | TRA1 | 1.17 | 1.52 |
| 201422_at | interferon, gamma-inducible protein 30 | IFI30 | 1.16 | 2.04 |
| 214439_x_at | bridging integrator 1 | BIN1 | 1.16 | 1.70 |
| 202838_at | fucosidase, alpha-L-1, tissue | FUCA1 | 1.14 | 1.30 |
| 204806_x_at | major histocompatibility complex, class I, F | HLA-F | 1.12 | 1.68 |
| 209295_at | TNF receptor superfamily, member 10b | TNFRSF10B | 1.09 | 1.43 |
| 209635_at | adaptor-related protein complex 1, sigma 1 subunit | AP1S1 | 1.06 | 1.53 |
| 203038_at | protein tyrosine phosphatase, receptor type, K | PTPRK | 1.04 | 1.39 |
| 218376_s_at | NEDD9 interacting protein | NICAL | 1.02 | 1.64 |
| 210776_x_at | transcription factor 3 | TCF3 | 1.01 | 1.46 |
| 217741_s_at | zinc finger protein 216 | ZNF216 | −1.02 | −1.49 |
| 213005_s_at | kidney ankyrin repeat-containing protein | KANK | −1.02 | −2.06 |
| 201851_at | SH3-domain GRB2-like 1 | SH3GL1 | −1.05 | −1.39 |
| 220942_x_at | growth and transformation-dependent protein | E2IG5 | −1.07 | −1.55 |
| 219100_at | hypothetical protein FLJ22559 | FLJ22559 | −1.07 | −1.77 |
| 218205_s_at | MAP kinase-interacting serine/threonine kinase 2 | MKNK2 | −1.10 | −1.29 |
| 220620_at | NICE-1 protein | NICE-1 | −1.10 | −2.37 |
| 218231_at | N-acetylglucosamine kinase | NAGK | −1.10 | −1.76 |
| 203585_at | zinc finger protein 185 (LIM domain) | ZNF185 | −1.12 | −2.57 |
| 203771_s_at | biliverdin reductase A | BLVRA | −1.14 | −1.79 |
| 219090_at | solute carrier family 24, member 3 | SLC24A3 | −1.15 | −2.02 |
| 219597_s_at | dual oxidase 1 | DUOX1 | −1.16 | −2.61 |
| 214279_s_at | NDRG family member 2 | NDRG2 | −1.18 | −2.37 |
| 219104_at | ring finger protein 141 | RNF141 | −1.18 | −2.12 |
| 209872_s_at | plakophilin 3 | PKP3 | −1.19 | −1.90 |
| 201848_s_at | BCL2/adenovirus E1B 19 kDa interacting protein 3 | BNIP3 | −1.22 | −1.92 |
| 55872_at | KIAA1196 protein | KIAA1196 | −1.23 | −1.45 |
| 57588_at | solute carrier family 24, member 3 | SLC24A3 | −1.23 | −1.85 |
| 212659_s_at | interleukin 1 receptor antagonist | IL1RN | −1.26 | −2.52 |
| 215440_s_at | hypothetical protein FLJ10097 | FLJ10097 | −1.28 | −1.89 |
| 207469_s_at | Pirin | PIR | −1.29 | −1.43 |
| 202575_at | cellular retinoic acid binding protein 2 | CRABP2 | −1.29 | −2.84 |
| 218935_at | EH-domain containing 3 | EHD3 | −1.30 | −2.39 |
| 210020_x_at | calmodulin-like 3 | CALML3 | −1.32 | −3.13 |
| 203126_at | inositol(myo)-1(or 4)-monophosphatase 2 | IMPA2 | −1.32 | −1.67 |
| 206004_at | transglutaminase 3 | TGM3 | −1.32 | −2.61 |
| 217508_s_at | hypothetical protein MGC12909 | MGC12909 | −1.36 | −1.94 |
| 209465_x_at | pleiotrophin | PTN | −1.37 | −2.00 |
| 210096_at | cytochrome P450, family 4, subfamily B, polypeptide 1 | CYP4B1 | −1.38 | −2.94 |
| 219983_at | HRAS-like suppressor | HRASLS | −1.39 | −1.73 |
| 219165_at | PDZ and LIM domain 2 (mystique) | PDLIM2 | −1.39 | −2.27 |
| 206400_at | lectin, galactoside-binding, soluble, 7 (galectin 7) | LGALS7 | −1.39 | −2.58 |
| 204454_at | leucine zipper, down-regulated in cancer 1 | LDOC1 | −1.44 | −1.22 |
| 221523_s_at | Ras-related GTP binding D | RRAGD | −1.44 | −2.13 |
| 219529_at | chloride intracellular channel 3 | CLIC3 | −1.45 | −2.61 |
| 208626_s_at | vesicle amine transport protein 1 homolog | VAT1 | −1.55 | −1.64 |
| 205623_at | aldehyde dehydrogenase 3 family, memberA1 | ALDH3A1 | −1.59 | −2.64 |
| 211737_x_at | pleiotrophin | PTN | −1.63 | −2.27 |

SUPPLEMENTAL TABLE 2-continued

| Probe set ID | Gene name | Gene symbol | Log2 R (B/N) | Log2 R (T/N) |
|---|---|---|---|---|
| 218484_at | NADH: ubiquinone oxidoreductase | LOC56901 | −1.69 | −2.66 |
| 221524_s_at | Ras-related GTP binding D | RRAGD | −1.72 | −2.42 |
| 220016_at | hypothetical protein MGC5395 | MGC5395 | −1.74 | −2.20 |
| 211734_s_at | Fc fragment of IgE, high affinity I, receptor | FCER1A | −2.03 | −2.82 |

REFERENCES

1. Stein H J, Siewert J R. Barrett's esophagus: pathogenesis, epidemiology, functional abnormalities, malignant degeneration, and surgical management. Dysphagia 1993; 8:276-88.
2. Lagergren J, Bergstrom R, Lindgren A, Nyren O. Symptomatic gastroesophageal reflux as a risk factor for esophageal adenocarcinoma. N Engl J Med 1999; 34:825-31.
3. Shaheen N, Ransohoff D F. Gastroesophageal reflux, Barrett esophagus and esophageal cancer. JAMA 2002; 287: 1972-81.
4. Shaheen N J, Crosby M A, Bozymski E M, Sandler R S. Is there publication bias in the reporting of cancer risk in Barrett's esophagus? Gastroenterology 2000; 119:333-8.
5. Devesa S S, Blot W J, Fraumeni J F Jr. Changing patterns in the incidence of esophageal and gastric carcinoma in the United States. Cancer 1998; 83:2049-53.
6. Swisher S G, Hunt K K, Holmes E C, Zinner M J, McFaddwn D W. Changes in the surgical management of esophageal cancer from 1970 to 1993. Am J Surg 1995; 169:609-14.
7. Goldblum J R, Lauwers G Y. Dysplasia arising in Barrett's esophagus: diagnostic pitfalls and natural history. Semin Diagn Pathol 2002; 19:12-19.
8. McManus D T, Olaru A, Meltzer S J. Biomarkers of esophageal adenocarcinoma and Barrett's esophagus. Cancer Res 2004; 64:1561-9.
9. Luo A, Kong J, Hu G, et al. Discovery of Ca2+-relevant and differentiation-associated genes downregulated in esophageal squamous cell carcinoma using cDNA microarray. Oncogene 2004; 23:1291.
10. Xu Y, Selaru F M, Yin J, et al. Artificial neural networks and gene filtering distinguish between global gene expression profiles of Barrett's esophagus and esophageal cancer. Cancer Res 2002; 62:3493-7.
11. Dahlberg P S, Ferrin L F, Grindle S M, et al. Gene expression profiles in esophageal adenocarcinoma. Ann Thorac Surg 2004; 77: 1008-15.
12. Barrett M T, Yeung K Y, Ruzzo W L, et al. Transcriptional analyses of Barrett's metaplasia and normal upper Gl mucosae. Neoplasia 2002; 4:121-8.
13. Williams R R, Broad S, Sheer D, Ragoussis J. Subchromosomal positioning of the epidermal differentiation complex (EDC) in keratinocyte and lymphoblast interphase nuclei. Exp Cell Res 2002; 272:163-75.
14. Marenholz I, Zirra M, Fischer D F, Backendorf C, Ziegler A, Mischke D. Identification of human epidermal differentiation complex (EDC)-encoded genes by subtractive hybridization of entire YACs to a gridded keratinocyte cDNA library. Genome Res 2001; 11:341-55.
15. Khodarev N N, Yu J, Nodzenski E, Murley J S, et al. Method of RNA purification from endothelial cells for DNA array experiments. Biotechniques 2002; 32:316-20.
16. Khodarev N N, Park J, Kataoka Y, et al. Receiver operating characteristic analysis: a general tool for DNA array data filtration and performance estimation. Genomics 2003; 81:202-209.
17. Khodarev N N, Beckett M, Labay E, Darga T, Roizman B, Weichselbaum R R. STAT1 is overexpressed in tumors selected for radioresistance and confers protection from radiation in transduced sensitive cells. Proc Natl Acad Sci USA 2004; 101:1714-9.
18. Tusher V G, Tibshirani R, Chu G. Significance analysis of microarrays applied to the ionizing radiation response. Proc Natl Acad Sci USA 2001; 98:5116-21.
19. Draghici S, Khatri P, Martins R P, Ostermeier G C, Krawetz S A. Global functional profiling of gene expression. Genomics 2003; 81:98-104.
20. Khodarev N N, Kataoka Y, Murley J S, Weichselbaum R R, Grdina D J. Interaction of amifostine and ionizing radiation on transcriptional patterns of apoptotic genes expressed in human microvascular endothelial cells (HMEC). Int J Radiat Oncol Biol Phys 2004; 60:553-63.

The invention claimed is:

1. A method of assessing risk of adenocarcinoma in a mammal with Barrett's esophagus comprising:
   (a) determining the ratio of the expression of GATA6 and SPRR3 in esophageal cells from the mammal; and
   (b) comparing the ratio of step (a) to the ratio of expression of GATA6 and SPRR3 in a reference selected from the group consisting of normal esophageal epithelium obtained from the mammal at the same or different time, cells characteristic of Barrett's esophagus obtained from the mammal at a different time, and a normal range established using normal esophageal epithelium obtained from a population of individuals, an increase in the ratio of step (a) relative to the ratio of the reference being indicative of increased risk of adenocarcinoma.

2. The method of claim 1, wherein the level of expression is measured by quantitative reverse transcription-PCR.

3. The method of claim 2, wherein the level of expression is measured by real time PCR.

4. The method of claim 1, wherein the reference is normal esophageal epithelium obtained from the mammal at essentially the same time as the Barrett's esophageal cells.

5. The method of claim 1, wherein the reference is normal esophageal epithelium or second Barrett's esophageal cells obtained from the mammal prior to obtaining the Barrett's esophageal cells of step (a).

6. The method of claim 1, wherein the reference is a panel of normal esophageal epithelium obtained from a population of mammals.

7. The method of claim 1, further comprising determining the expression of a marker selected from the group consisting of HOXB7, TCF3, S100A2, and SCCA.

* * * * *

SEQUENCE LISTING

<160> NUMBER OF SEQ ID NOS: 14

<210> SEQ ID NO 1
<211> LENGTH: 20
<212> TYPE: DNA
<213> ORGANISM: Artificial
<220> FEATURE:
<223> OTHER INFORMATION: Synthetic oligonucleotide

<400> SEQUENCE: 1
tgcaccacca actgcttagc                                            20

```
<210> SEQ ID NO 2
<211> LENGTH: 21
<212> TYPE: DNA
<213> ORGANISM: Artificial
<220> FEATURE:
<223> OTHER INFORMATION: Synthetic oligonucleotide

<400> SEQUENCE: 2
ggcatggact gtggtcatga g                                                 21

<210> SEQ ID NO 3
<211> LENGTH: 18
<212> TYPE: DNA
<213> ORGANISM: Artificial
<220> FEATURE:
<223> OTHER INFORMATION: Synthetic oligonucleotide

<400> SEQUENCE: 3
agcgcgtgcc ttcatcac                                                     18

<210> SEQ ID NO 4
<211> LENGTH: 18
<212> TYPE: DNA
<213> ORGANISM: Artificial
<220> FEATURE:
<223> OTHER INFORMATION: Synthetic oligonucleotide

<400> SEQUENCE: 4
gcaagtggtc tgggcacc                                                     18

<210> SEQ ID NO 5
<211> LENGTH: 19
<212> TYPE: DNA
<213> ORGANISM: Artificial
<220> FEATURE:
<223> OTHER INFORMATION: Synthetic oligonucleotide

<400> SEQUENCE: 5
ggatctaccc ctggatgcg                                                    19

<210> SEQ ID NO 6
<211> LENGTH: 20
<212> TYPE: DNA
<213> ORGANISM: Artificial
<220> FEATURE:
<223> OTHER INFORMATION: Synthetic oligonucleotide

<400> SEQUENCE: 6
gtctttccgt gaggcagagc                                                   20

<210> SEQ ID NO 7
<211> LENGTH: 20
<212> TYPE: DNA
<213> ORGANISM: Artificial
<220> FEATURE:
<223> OTHER INFORMATION: Synthetic oligonucleotide

<400> SEQUENCE: 7
ctgtctctgc cacctggtct                                                   20

<210> SEQ ID NO 8
<211> LENGTH: 21
<212> TYPE: DNA
<213> ORGANISM: Artificial
<220> FEATURE:
<223> OTHER INFORMATION: Synthetic oligonucleotide
```

-continued

```
<400> SEQUENCE: 8
ctcaaaggca tcaacagtcc t                                              21

<210> SEQ ID NO 9
<211> LENGTH: 20
<212> TYPE: DNA
<213> ORGANISM: Artificial
<220> FEATURE:
<223> OTHER INFORMATION: Synthetic oligonucleotide

<400> SEQUENCE: 9
ttcatgttcg acctgttcca                                                20

<210> SEQ ID NO 10
<211> LENGTH: 20
<212> TYPE: DNA
<213> ORGANISM: Artificial
<220> FEATURE:
<223> OTHER INFORMATION: Synthetic oligonucleotide

<400> SEQUENCE: 10
gcagcttttc ctgtggtgtt                                                20

<210> SEQ ID NO 11
<211> LENGTH: 20
<212> TYPE: DNA
<213> ORGANISM: Artificial
<220> FEATURE:
<223> OTHER INFORMATION: Synthetic oligonucleotide

<400> SEQUENCE: 11
atccctgagc agctgaagac                                                20

<210> SEQ ID NO 12
<211> LENGTH: 20
<212> TYPE: DNA
<213> ORGANISM: Artificial
<220> FEATURE:
<223> OTHER INFORMATION: Synthetic oligonucleotide

<400> SEQUENCE: 12
ctgctgttga agctgaggtg                                                20

<210> SEQ ID NO 13
<211> LENGTH: 20
<212> TYPE: DNA
<213> ORGANISM: Artificial
<220> FEATURE:
<223> OTHER INFORMATION: Synthetic oligonucleotide

<400> SEQUENCE: 13
gtgacatcaa cgaggccttt                                                20

<210> SEQ ID NO 14
<211> LENGTH: 20
<212> TYPE: DNA
<213> ORGANISM: Artificial
<220> FEATURE:
<223> OTHER INFORMATION: Synthetic oligonucleotide

<400> SEQUENCE: 14
ctgctttggg attcaggttc                                                20
```